United States Patent [19]

Wissler

[11] Patent Number: 4,495,096

[45] Date of Patent: Jan. 22, 1985

[54] PROCESS FOR PRODUCING AND OBTAINING ANAPHYLATOXIN-AND COCYTOTAXIN-CONTAINING LEUCOTAXINE PREPARATIONS AND OF ANAPHYLATOXIN AND COCYTOTAXIN PROTEINS IN MOLECULARLY HOMOGENEOUS, BIOLOGICALLY ACTIVE FORM

[75] Inventor: Josef H. Wissler, Bad Nauheim, Fed. Rep. of Germany

[73] Assignee: Max-Planck Gesellschaft Zur Forderung der Wissenchaften, Gottingen, Fed. Rep. of Germany

[21] Appl. No.: 275,014

[22] Filed: Jun. 18, 1981

[30] Foreign Application Priority Data

Jun. 19, 1980 [DE] Fed. Rep. of Germany ....... 3022914

[51] Int. Cl.$^3$ ............ C07G 7/00

[52] U.S. Cl. ............ 260/112 B; 435/68; 435/69; 424/101

[58] Field of Search ............ 260/112 B; 424/101, 424/177; 435/68, 69

[56] References Cited

PUBLICATIONS

Tack, B. F. et al., Biochemistry, vol. 15, No. 20, pp. 4513–4521, 1976.

Wissler, J., Eur. J. Immunol. vol. 2, pp. 73–96, 1972.

Vallota, E., J. Exp. Med., vol. 137, pp. 1109–1123, 1973.

Gerard, C., J. Biol. Chem., vol. 254, pp. 6346–6351, 1979.

Conroy, M., J. Immunol., vol. 116, pp. 1682–1687, 1976.

Fernandez, H., J. Immunol., vol. 120, pp. 109–115, 1978.

*Primary Examiner*—John C. Bleutge

*Assistant Examiner*—Patricia Short

*Attorney, Agent, or Firm*—Cooper, Dunham, Clark, Griffin & Moran

[57] ABSTRACT

The invention relates to a process for producing and obtaining anaphylatoxin- and cocytotaxin-containing leucotaxine preparations and anaphylatoxin and cocytotaxin proteins in molecularly homogeneous, biologically active form from contact-activated mammalian serum by the following steps:

separation of the proteins from other serum constituents to obtain a serum protein concentrate fraction, separation of a part of accompanying foreign blood proteins from anaphylatoxin and cocytotaxin present in the said protein concentrate fraction, isolation of the leucotaxine preparation by chromatography on hydroxyapatite, and optionally further purification and/or separation of the leucotaxine preparation into anaphylatoxin and cocytotaxin proteins by chromatographical methods.

The invention is characterized in that, prior to chromatography on hydroxyapatite, in the above-mentioned process, a major fraction of accompanying foreign blood constituents is separated from the said serum protein concentrate fraction by fractional elution and/or precipitation with a water-soluble alcohol and/or at least one molecular sieve filtration.

32 Claims, 13 Drawing Figures

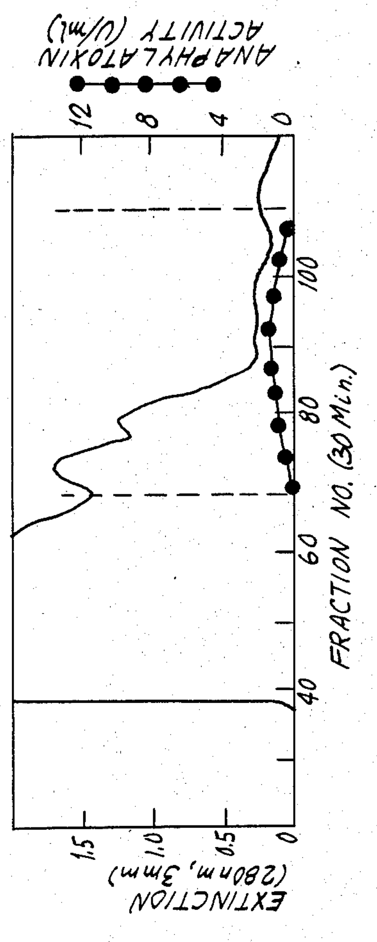

FIG. 1 EXAMPLE B6

FIRST PREPARATIVE MOLECULAR SIEVE FILTRATION OF THE LEUCOTAXINE PREPARATION (ISOLATED FROM THE SERUM PROTEIN CONCENTRATE FRACTION (EXAMPLE A) AND BY A FRACTIONAL ELUTION STEP FOR REMOVAL OF A FRACTION OF CONTAMINATING FOREIGN PROTEINS

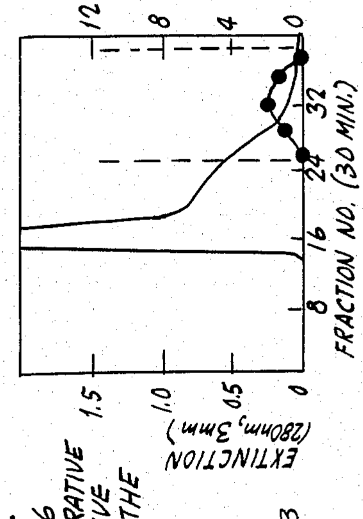

FIG. 2

EXAMPLE B6

SECOND PREPARATIVE MOLECULAR SIEVE FILTRATION OF THE LEUCOTAXINE PREPARATION

SEE FIG. 3

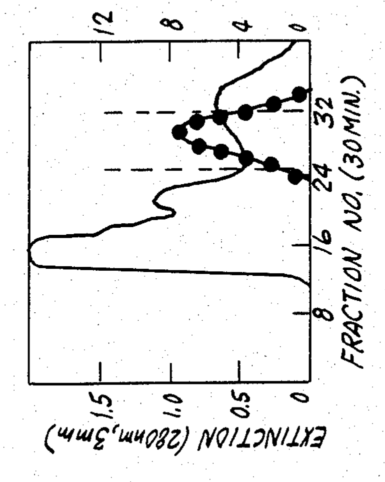

FIG. 3

EXAMPLE B6

ANALYTICAL MOLECULAR SIEVE FILTRATION OF THE LEUCOTAXINE PREPARATION

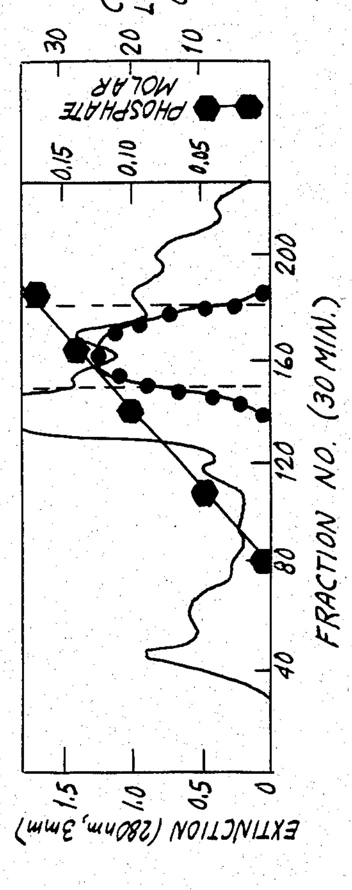

FIG. 4 EXAMPLE C1

CHROMOTOGRAPHY OF THE LEUCOTAXINE PREPARATION ON HYDROXYAPATITE

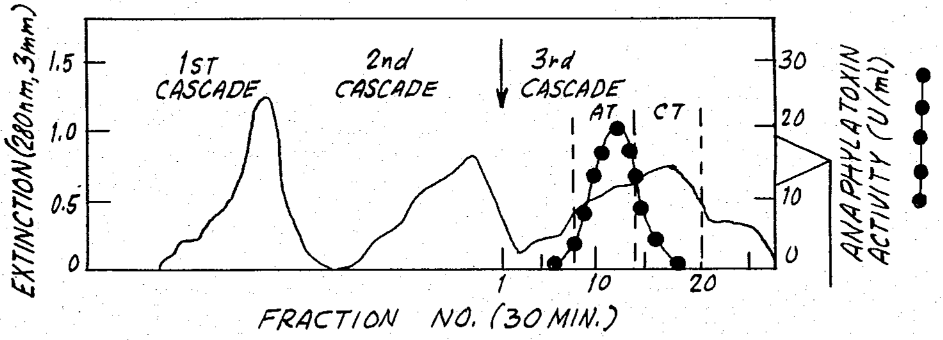

FIG. 5 EXAMPLE C5
ANALYTICAL MOLECULAR SIEVE FILTRATION CASCADE CHROMATOGRAPHY FOR SEPARATION OF THE LEUCOTAXINE PREPARATION INTO ANAPHYLATOXIN (AT) AND COCYTOTAXIN (CT)

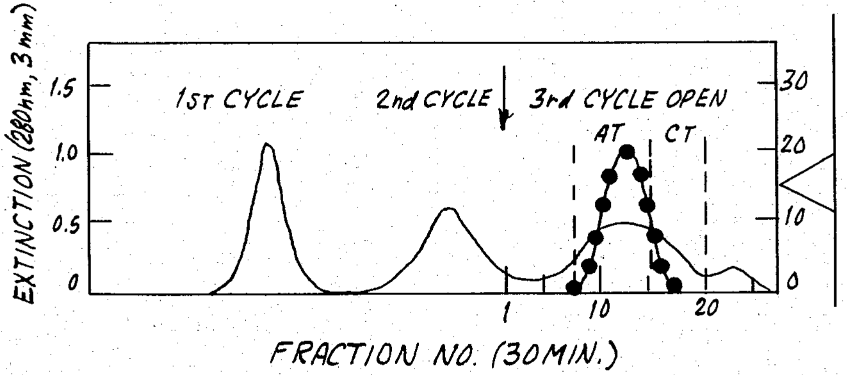

FIG. 6 EXAMPLE C5
ANALYTICAL MOLECULAR SIEVE RECYCLING CHROMATOGRAPHY FOR FURTHER PURIFICATION OF ANAPHYLATOXIN

CONTINUATION: FINAL PURIFICATION SEQUENCE FOR ANAPHYLATOXIN AT

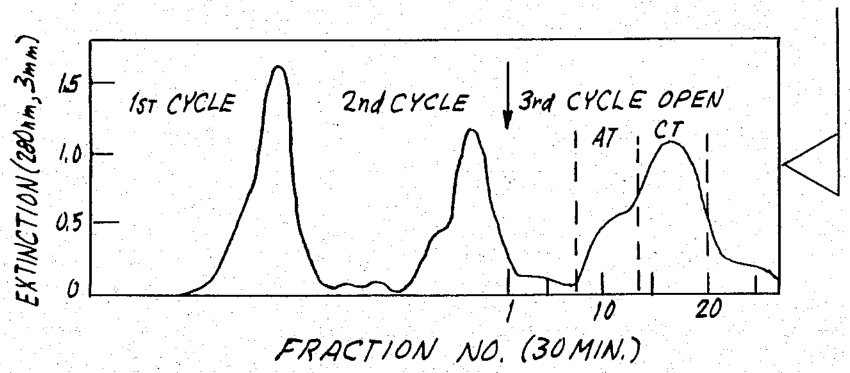

FIG. 7 EXAMPLE C5
ANALYTICAL MOLECULAR SIEVE RECYCLING CHROMATOGRAPHY FOR FURTHER PURIFICATION OF COCYTOTAXIN

CONTINUATION: FINAL PURIFICATION SEQUENCE FOR COCYTOTAXIN FIGS. 11-13 CT

FIG. 8 EXAMPLE C5
FINAL PURIFICATION OF ANAPHYLATOXIN, 1st. STAGE: RECHROMATOGRAPHY ON HYDROXYAPATITE FOLLOWING STEP OF FIG. 6 ◁ AT
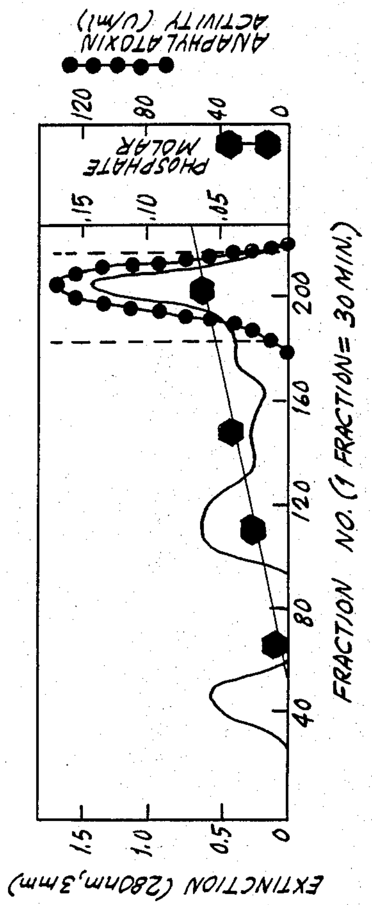
FIG. 9 EXAMPLE C5
FINAL PURIFICATION OF ANAPHYLATOXIN, 2nd STAGE: ANALYTICAL ZONE-PRECIPITATION CHROMATOGRAPHY
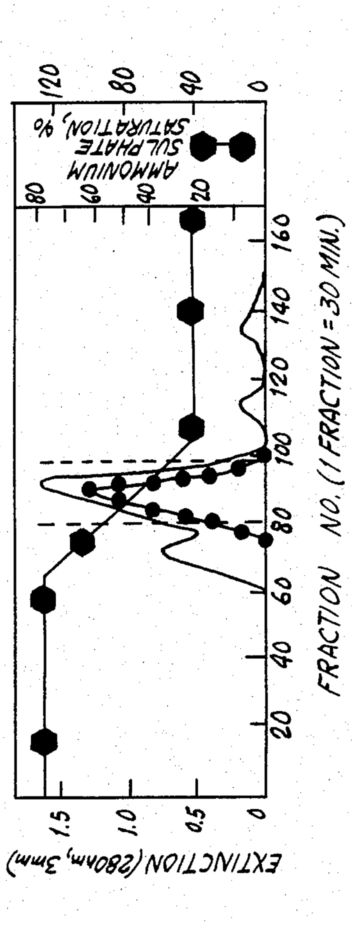
FIG. 10 EXAMPLE C5
FINAL PURIFICATION OF ANAPHYLATOXIN, 3rd STAGE; ANALYTICAL MOLECULAR SIEVE FILTRATION
AT
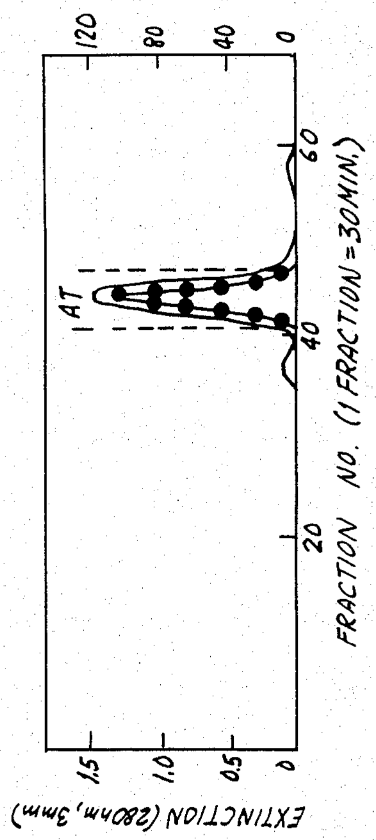

FIG. 11 EXAMPLE C5
FINAL PURIFICATION OF COCYTOTAXIN, 1st. STAGE: RECHROMATOGRAPHY ON HYDROXYAPATITE FOLLOWING STEP OF FIG. 7
CT
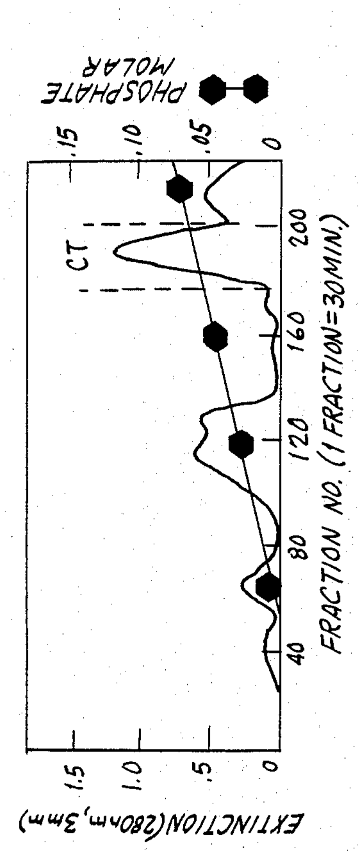
FIG. 12 EXAMPLE C5
FINAL PURIFICATION OF COCYTOTAXIN, 2nd STAGE: ANALYTICAL ZONE-PRECIPITATION CHROMATOGRAPHY
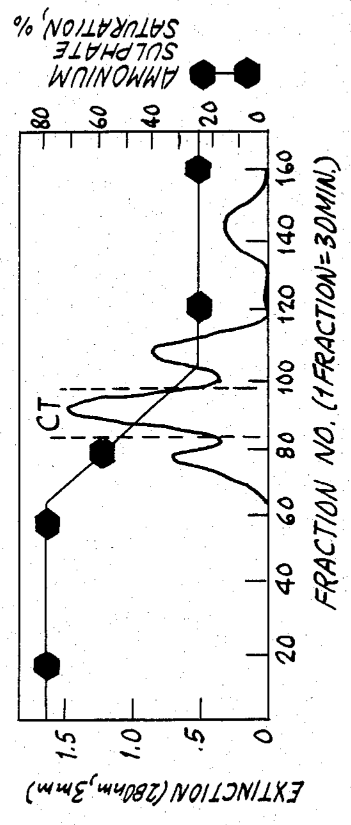
FIG. 13 EXAMPLE C5
FINAL PURIFICATION OF COCYTOTAXIN, 3rd STAGE: ANALYTICAL MOLECULAR SIEVE FILTRATION
CT
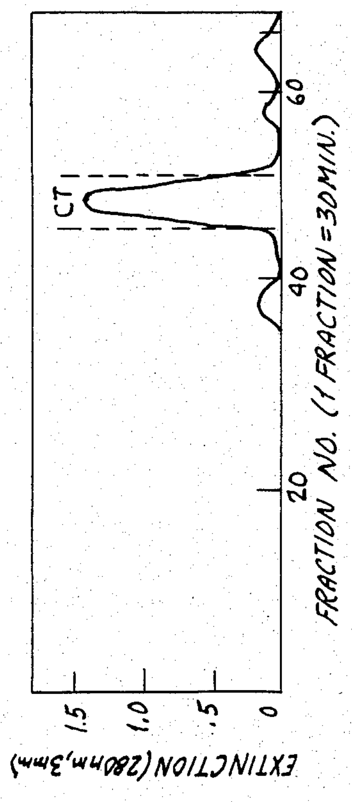

PROCESS FOR PRODUCING AND OBTAINING ANAPHYLATOXIN-AND COCYTOTAXIN-CONTAINING LEUCOTAXINE PREPARATIONS AND OF ANAPHYLATOXIN AND COCYTOTAXIN PROTEINS IN MOLECULARLY HOMOGENEOUS, BIOLOGICALLY ACTIVE FORM

BACKGROUND OF THE INVENTION

The present invention relates to a method of separating blood components. More specifically it relates to a method of producing and obtaining anaphylatoxin- and cocytotaxin-containing leucotaxine preparations and of anaphylatoxin and cocytotaxin proteins in molecularly homogeneous, biologically active form.

Destruction of tissue in inflammation induced by non-immunological and/or immunological processes leads to formation of a variety of endogenous substances (mediators and hormones). They regulate the complex individual steps of activation of inflammation and tissue repair processes. The mediators are produced either as humoral mediators by limited and regulated proteolysis of plasma or serum proteins, or they are released as cellular mediators by active secretion and/or cell lysis from cells and tissues. They form part of the body's defensive system, which systemic and local activation they play part. They thus contribute to removal and detoxification of destroyed endogenous substances and/or invaded foreign bodies. In addition, by regulation of the cell-division and tissue growth processes in wound healing, they participate in restoration of the physiological structures and functions of the organism. Like the classical hormones of the endocrinal glands, inflammatory mediators are trace substances, that are present in situ in only minute concentrations in tissue or blood.

By activation of the kinin system, the coagulation system, the complement system, and also of other blood-protein and cell factors, a variety of mediators may be produced concurrently or sequentially which are responsible for the apparent biological activities of activated serum. Amongst them to mention are chemical attraction of leucocytes (leucotaxis), immunoadherence and the smooth muscle concentrtion. Anaphylatoxin and cocytotaxin are among the blood protein mediators formed by limited, regulated proteolysis of plasma and serum factors in concurrence with complement system activation. They play a major role in the chemical attraction of leucocytes. In addition, anaphylatoxin also possesses pharmacological properties and cardiovascular effects on account of its spasmogenic effects on muscle cells.

Anaphylatoxin was discovered after treating mammalian sera with antigen-antibody complexes; cf. E. Friedberger, Z Immunitätsforsch. 4 (1919), p. 636–689. It is considered as one of the fragments (C5a) of the fifth complement component, with which it has many biological activities in common; cf. J. Jensen, Science 155 (1967), p. 1122–1123. There is still no proof of their chemical identity. Formation of anaphylatoxin and other mediators can be induced by contact reactions of mammalian blood, plasma, or serum with various hydrophilic, insoluble high-molecular substances, such as dextran, yeast, and also with bacterial endotoxins (lipopolysaccharides). Application of such modified sera in vivo and in vitro induces various types of biological effects. Amongst them to mention are the typical anaphylatoxin effects and other reactions which are similar to, or comparable with in vivo immune and non-immune processes apparent in allergy and tissue damage reactions. These biological reactions in particular include release of histamine, lethal shock, contraction of the smooth muscles, and chemotactic activity for neutrophil and eosinophil leucocytes.

A process of ten steps for obtaining anaphylatoxin from rat, pig and guinea-pig serum treated with dextran, yeast or immune complexes, has been described by J. H. Wissler in Eur. J. Immunol. 2(1972), pp. 73--96 and in Int. Arch. Allergy 32 (1972), pp. 722–747. According to this known process, anaphylatoxin is separated from accompanying foreign proteins by chromatography on hydroxyapatite. Prior to this step, an anaphylatoxin-containing crude protein fraction of contact-activiated serum is separated off by cation exchange reaction from the supernatant, negatively absorbed serum components. The anaphylatoxin-containing protein eluate obtained by the cation exchange reaction is concentrated by salting-out precipitation of proteins with ammonium sulfate (serum protein concentrate fraction). Prior to chromatography on hydroxyapatite part of the foreign substances, including a small fraction of accompanying foreign proteins, are removed by treatment with calcium phosphate gel. Following chromatography on hydroxyapatite further purification of anaphylatoxin in carried out in this known process by molecular sieve chromatography, ion-exchange chromatography on hydroxyapatite, and gel-permeation chromatography. Anaphylatoxin is finally obtained in crystalline form in a molecularly homogenous, biologically active state.

By the above process, the anaphylatoxin-containing protein preparation obtained by chromatography on hydroxyapatite, which is chemotactically active for neutrophil leucocytes, is separated into two main protein components. The one protein thus obtained has the classical properties of anaphylatoxin. For example, in vivo it causes release of histamine and it induces the typical lethal anaphylatoxin shock by contraction of the smooth muscles. This substance (classical anaphylatoxin) which is obtained in crystalline form by the known process, however has no appreciable chemotactic activity on neutrophilic leucocytes. This activity is formed by the activation process in crude serum in concurrence with anaphylatoxin activity, as are other activities.

The second protein, termed cocytotaxin, is likewise obtained by the known process in a crystalline state; cf. J. H. Wissler, Eur. J. Immunol. 2 (1972), pp. 84–89. The physicochemical properties of cocytotaxin are similar to anaphylatoxin. But biologically, it is different. Cocytotaxin has no spasmogenic activity of anaphylatoxin. However, as anaphylatoxin, cocytotaxin has no appreciable chemotactic activity on neutrophilic leucocytes.

Recombination of anaphylatoxin and cocytotaxin in various molar ratios in vitro leads to a restoration of the chemotactic activity for neutrophil leucocytes intrinsic to contact-activated crude serum. Thus, anaphylatoxin and cocytotaxin together constitute a leucotaxine preparation as a binary protein system which is biologically active in vitro and in vivo. In this system anaphylatoxin is the activity principle and cocytotaxin constitutes the activity-inducing cofactor (cochemotaxin). Both separated proteins, anaphylatoxin and cocytotaxin, and the leucotaxine preparation containing the two substances as a biologically active binary protein system are valuable substances with a wide array of application possibilities in pathology and immunology. For example, they may be used to induce desired focal inflammation processes, e.g. in tumours ("biochemical surgery"). Accumulating leucocytes can be regulated to be composited of selected cell patterns. In addition, by accumulating selective patterns of leucocyte types they can serve for formation, in statu nascendi, of substances with cell-specific action promoting and inhibiting cell division produced by leucocytes at the reaction site of inflammation. Furthermore, they can be used to increase, in statu nascendi, the immune status at a reaction site in tissue, or tumour sites by immunopotentiators secreted by attracted and accumulating leucocyte populations.

In general, purification processes for proteins and other natural substances consist of a sequence of combined separation techniques. Subtle differences in molecular size, charge, form, structure, stability, and nature of the molecule surface between the desired natural substance and the accompanying foreign substances are used in such steps for separation. Accordingly, a large number of combinations of various separation techniques can be worked out for purification of a protein. The nature and the conditions of separation steps used, but as well thier sequential combination, are of paramount significance for operational properties, technical practicability, optional automatisation possibility and economics of a purification process and for yield and molecular quality of the natural product investigated. Particular attention has to be focused on optimum form of separation steps and on their ingenious combination into a purification sequence within a frame of structural and functional stability and other molecular parameters of the substance under investigation. This implies that use of identical or similar separation principles (e.g. molecular sieve filtration, dialysis ion-exchange absorption, etc.) in a different combination can be of decisive and paramount importance for practice and economics of a purification process and yield and quality of the product obtained. In some cases, use or omission of a single technique (e.g. hydroxyapatite chromatography, zone-precipitation chromatography, etc.) at a certain position in the purification sequence, or within a partial sequence, is decisively significant for yield and quality of the desired natural product as well as for practice and economics of the purification process. These general relationships and basic principles inherent to purification processes of natural products are clearly illustrated e.g. by some well known facts. Thus, within an economically and technically operable process for the purification of a natural product, initial dialysis or lyophilizaton steps are not recommended prior to reduction of initial volumes of the crude extract by a factor ofat least 500-1000 through other techniques.

As above-mentioned, mediators as anaphylatoxin and cocytotaxin are trace substances occurring only in very small quantities in the prepared serum. 100 liters of contact-activated serum (corresponding to 250-300 liters of blood) contain about 7 to 8 kg of protein in addition to other substances. Only about 0,3 to 1,5 g of this protein mass (depending on the species and on the nature of the contact reaction) represent anaphylatoxin, cocytotaxin being present in about twice to three times this quantity. Of this, a maximum of 10 to 20% of each protein can be isolated, since any purification is a complex process having only restricted yields. Therefore, a prerequisite for the practical use of these proteins is their isolation in appreciable quantities. Hence, very large volumes of blood have to be processed.

The above-mentioned process is not suitable for this purpose. Use of hydroxyapatite for structure-conserving purification of these proteins is decisively important. For technical and economic reasons, however, it is not possible to chromatography large volumes of protein solutions on hydroxyapatite columns. Larger amounts of proteins tend to support the strong tendency of hydroxyapatite to block up. Furthermore hydroxyapatite is very expensive. Its use on large scales is not economical. Separation of a part of accompanying foreign proteins achieved in the known process by absorption on calcium phosphate gel admittedly causes a reduction by about 10% of the amount of foreign substance. This reduction is too small to be of practical importance in large scale preparation of these mediators. Thus, the residual volume of protein solution to be applied on the hydroxyapatite column is still too large for economical processing of larger quantities of blood. According to the known process, under optimum conditions, a volume reduction of 1000 ml serum to a minimum of some 25 ml of protein solution can be achieved prior to its application onto the hydroxyapatite column.

Another process for preparation of anaphylatoxin has been described by M. Liefländer et al. in Hoppe-Seyler's Z. Physiol. Chem. 353 (1972), pp. 385-392. Anaphylatoxin is separated from the foreign proteins by repeated cation-exchange chromatography and molecular sieve filtration combined with lyophilization and dialysis steps. Some of the steps are performed in organic solvents and in unbuffered acid solution. E. H. Vallota and H. J. Müller-Eberhardt described a modification of this technique in J. Exp. Med. 137 (1973), pp. 1109-1123, as did H. N. Fernadez et al. in J. Immunol. 120 (1978), pp. 109-115, in which a further cation-exchange chromatographic step and an additional anion-exchange chromatographic step are included. Finally, in J. Biol. Chem. 251 (1979), pp. 6346-6351, C. Gerald and T. E. Hugli suggested another modification of this process for isolation of anaphylatoxin, in which the activated crude serum was first adjusted to pH 0 (1 mol/1 HCl). Without experimental proof, it is implied that these unphysiological conditions do jeopardize the natural biological quality of products investigated. They claimed that 65% of the foreign proteins are precipitated (no experimental data are given). The residual protein fraction is purified further by a molecular sieve filtration, cation-exchange positive absorption chromatography, and anion-exchange negative absorption chromatography.

The above-mentioned known processes are also unsuitable for economical isolation of anaphylatoxin in such quantities as are needed for practical purposes. The use of large volumes of serum would demand too large and too bulky column capacities and almost extremly awkward dialysis and lyophilization steps. In fact, these processes too were conceived and published only for use of relatively small initial serum volumes (from 0.5 to a maximum of 10 liters of contact-activated serum). Moreover, these processes have the disadvantage that irreversible damage of protein structure as a result of the drastic, non-physiological conditions (organic, non-aqueous solvents; pH 0) cannot be excluded or are not investigated, also such events are most likely; see for example J. H. Wissler in Proc. Immunosymposium, Vienna 1973, Springer Verlag Vienna 1975, pp.

91–105. The isolation of cocytotaxin and the separation of residual trace contaminants of other foreign proteins which electrophoretically are hardly detectable, but which are chromatographically obvious, are not envisaged in this method; although their presence is most likely; cf. H. N. Fernandez at al. (op. cit.) and M. C. Conroy et al. in J. Immunol 116 (1976), pp. 1682–1687.

It is therefore, a primary object of this invention to provide a process for producing and obtaining anaphylatoxin- and cocytotaxin-containing leucotaxine preparations from large amounts of blood.

It is another object of this invention to provide a process for producing and obtaining anaphylatoxin and cocytotaxin proteins in molecularly homegenous form.

It is another object of this invention to provide a process for producing and obtaining anaphylatoxin- and cocytotaxin-containing leucotaxine preparations and anaphylatoxin and cocytotaxin proteins in biologically active form.

It is still another object of this invention to provide a process for producing and obtaining anaphylatoxin-and cocytotaxin-containing leucotaxin preparations and anaphylatoxin and cocytotaxin proteins in appreciable quantities in their native intact structure.

It is still another object of this invention to provide a process for producing and obtaining anaphylatoxin- and cocytotaxin-containing leucotaxine preparations and anaphylatoxin and cocytotaxin proteins in a relatively simple, automatable and economical manner.

These and other objects and advantages of the present invention will be evident from the following description of the invention.

SUMMARY OF THE INVENTION

The invention is based on a process for producing and obtaining anaphylatoxin- and cocytotaxin-containing leucotaxine preparations and anaphylatoxin and cocytotaxin proteins in molecularly homogeneous, biologically active form from contact-activated mammalian serum by:

separation of the proteins from other serum constituents to obtain a serum protein concentrate fraction, separation of a part of accompanying foreign blood proteins from anaphylatoxin and cocytotaxin present in the said protein concentrated fraction, isolation of the leucotaxine preparation by chromatography on hydroxyapatite, and optionally further purification and/or separation of the leucotaxine preparation into anaphylatoxin and cocytotaxin proteins by chromatographical methods.

The invention is characterized in that, prior to chromatography on hydroxyapatite, in the above-mentioned process, a major fraction of accompanying foreign blood constituents is separated from the said serum protein concentrate fraction by fractional elution and/or precipitation with a water-soluble alcohol and/or at least one molecular sieve filtration.

DETAILED DESCRIPTION OF THE INVENTION

The process in accordance with the invention allows processing of large amounts of serum and thus the fast and enconomical isolation of appreciable quantities of anaphylatoxin and cocytotaxin. In accordance with the invention, the major part of the accompanying foreign proteins is removed prior to chromatography on hydroxyapatite, which is a critical step for anaphylatoxin and cocytotaxin qualities. Thus, only a small fraction (in the preferred embodiments less than about 0.09%) of the total amount of serum proteins are to be applied to the hydroxyapatite column. A batch can be started for example at least with 100 to 200 liters of contact-activated serum (about 300 to 600 liters of blood). For example with 100 liters of contact-activated serum, the protein solution volume still containing all the anaphylatoxin and cocytotaxin can be reduced to less than about 100 to 200 ml, which represents a volume reduction factor of about 500–1000, prior to use of hydroxyapatite. In addition, the process allows to obtain the investigated mediators in their native, biologically active conformation.

The process for production of a leucotaxine preparation containing anaphylatoxin and cocytotaxin and also anaphylatoxin and cocytotaxin proteins will now be specifically explained in detail.

A. PRODUCTION OF ANAPHYLATOXIN AND COCYTOTAXIN IN SERUM. SEPARATION OF AN ANAPHYLYTOXIN AND COCYTOTAXIN-CONTAINING SERUM PROTEIN CONCENTRATE FRACTION FROM THE OTHER SERUM CONSTITUENTS

The product of anaphylatoxin and cocytotaxin in serum, for example by contact activation, the separation of the serum protein concentrate fraction from other serum constituents by aid of a cation-exchanger, elution of the absorbed protein fraction from the ion-exchanger, and concentration of proteins in the eluate obtained by salting out precipitation with ammonium sulfate is essentially carried out in the known manner; cf. J. H. Wissler, Eur. J. Immunol. 2 (1972), pp. 73–83.

Initial, crude material for the isolation of anaphylatoxin- and cocytotaxin-containing leucotaxin preparation and of anaphylatoxin and cocytotaxin (for brevity reasons the substances investigated will be referred to by the abbreviations AT and CT) in accordance with the process of the invention is mammalian serum. Because of its ready availability, human, bovine, equine, porcine, ovine, canine, feline, rabbit, rat and guinea-pig serum is preferred. The serum is obtained in the normal way by coagulation of blood and separation of the blood clot, for example by filtration and/or centrifugation, and is incubated for the formation of AT and CT, for example with dextran, yeast, or with the immune complex in conventional manner. After a sufficient period of incubation, for example in case of dextran about 1 h at 37° C., the incubated, contact-activated serum is cooled to a temperature of about 0° to 8° C. Then, the insoluble contact substance added for incubation is separated from the contact-activated, AT and CT-containing serum.

The incubated, contact-activated serum containing AT and CT is now treated with a cation-exchanger to separate the majority of proteins from other serum constituents. An example of a cation-exchanger suitable for this purpose are dextrans cross-linked with epichlorohydrin (Sephadex). It is preferable to use a weakly acidic cation-exchanger such as CM Sephadex C-50 and to perform the treatment at a pH of 4 to 6. To facilitate the charge process, the contact-activated serum can be diluted with a protein-compatible salt solution before treatment with the cation-exchanger. This salt solution can be used at the same time to adjust the pH. A special example of a salt solution for this purpose is a 0.001 mol/1 potassium phosphate-acetate buffer containing 0.2 mol/1 NaCl and having a pH of 4.5.

The cation-exchanger is added to the serum in sufficient quantity to absorb the main protein fraction of serum. As a rule about 1 volume of swollen ion-exchanger per volume of the serum is sufficient for this purpose. The supernatant is then separated from the cation-exchanger charged with the proteins, for example by decantation of centrifugation. The charged cation-exchanger is freed from the adhering, negatively absorbed serum components by washing with water or a salt solution. Preferably a pH of about 4 to 5 and a maximum temperature of about 15° C. is used. A special example of a salt solution suitable for the wash-out process is the mentioned potassium phosphate-acetate buffer having a pH of 4.5.

The protein-charged cation-exchanger is now eluted with a protein-compatible aqueous salt solution. A salt solution of high ionic strength with a pH of about 4 to 10 is preferably used for this purpose. Special examples for salt solutions of this kind are aqueous 0.5 mol/1 solution of potassium phosphate of pH 6.5 to 7.5 or a 2 to 5 mol/l solution chloride of the same pH.

The eluate obtained containing the bulk of serum proteins and AT and CT is now concentrated prior to subsequent separation of proteins. This concentration process which separates the bulk of aqueous salt solution from the proteins, can be done in various ways. For example, all the proteins can be precipitated by adjusting the eluate to an ammonium sulfonate concentration of about 3.7 mol/1 (salting-out precipitation). For this purpose, ammonium sulfate is added in a quantity of approximately 630 g/l eluate (saturation about 90%). During this process, the pH is preferably kept at about 4 to 9. The precipitated proteins are then separated from the almost protein-free supernatent, for example by decantation or centrifugation.

The eluate of the cation-exchange process can also be concentrated by using other methods, for example ultrafiltration or lyophilization. But these processes are time-consuming and relatively expensive. In this case for further performance in accordance with the process of the invention, however, the protein concentrate obtained must likewise be adjusted to an ammonium sulfate concentration of 3.7 mol/l.

In all cases, the AT- and CT-containing protein precipitate formed (serum protein concentrate fraction) is obtained in form of a protein mud. For purpose of further purification of AT and CT, this mud is used as such in the manner described below.

B. CRUDE PURIFICATION OF AT AND CT: SEPARATION OF THE BULK OF THE ACCOMPANYING FOREIGN PROTEINS OF AT AND CT

PREPARATION OF A AT- AND CT- CONTAINING "CRUDE LEUCOTAXINE PREPARATION".

In the known process (J. H. Wissler, Eur. J. Immunol 2 (1972), pp. 73–83), separation of accompanying foreign proteins and some other substances, such as lipids, from AT and CT in the serum protein concentrate fraction obtained in step A occurred only to a very small extent (maximum about 5–10%) by absorption on calcium phosphate gel. The remaining volume concentrated of protein solution from which the desired substances are to be obtained by chromatography on hydroxyapatite, therefore, is still relatively very large. Thus, only a small quantity of serum can be processed. In addition, the involved dialysis step necessary for this purpose is difficult to perform for larger volumes. Additionally some loss of the product occurs.

An outstanding characteristic of the process of the invention is, therefore, the first possibility to separate the major bulk (in the preferred embodiments more than 99.91%) of the accompanying foreign proteins from AT and CT prior to their chromatography on hydroxyapatite, which is critical for product quality, handling of the purification, process and economics. In this way, a large reduction of the quantity of protein to be processed can be achieved prior to this step of the process. In accordance with the invention the separation of the foreign proteins from the serum protein concentrate fraction is achieved by fractional elution and/or precipitation with a water-soluble alcohol and/or at least one molecular sieve filtration.

It is possible to remove a considerable amount of accompanying foreign proteins by only one performance of one of the purification methods in accordance with the invention. Thus, a satisfactory volume reduction of the serum protein concentrate fraction is achieved prior to charge of the hydroxyapatite column. For example, in the physiological pH range about 30% of the accompanying foreign proteins can be removed by fractional elution, about 60 to 70% by precipitation with a water-soluble alcohol, and up to 90% by molecular sieve filtration. However, as a property of polyelectrolytes, proteins of the serum protein concentrate fraction tend to adhere very strongly together. Furthermore, no ideal equilibria and distributions are obtained with marcromolecular polyelectrolytes as are proteins. Therefore, for example in spite of different molecular weights of proteins, by molecular sieve filtration no complete (ideal) separation according to their molecular weight proper is obtained at once. Hence, it is necessary to perform at least two of the said separation processes in sequence. Thus, preferably the serum protein concentrate fraction is, for example, first fractionally eluted and then subjected to a molecular sieve filtration. Or, the foreign proteins are first precipitated with a water-soluble alcohol, and, then, a molecular sieve filtration is carried out. Moreover, combinations of fractional elution and/or precipitation with a water-soluble alcohol with at least one preparative and one analytical molecular sieve filtration is preferred. All these combinations of the mentioned separation steps constitute objects of the invention. It is evident, that certain sequences of separation steps are of less advantage than other combinations. Thus, for example, it is imperative to perform a preparative molecular sieve filtration before an analytical molecular sieve filtration: In reverse order of performance difficulties in handling economics and yield are obvious.

Particularly preferred embodiments of the process in accordance with the invention consist of the following combinations of separation techniques:

(a) a fractional elution step followed by two preparative and then one analytical molecular sieve filtration;

(b) a fractional elution step followed by one protein precipitation step with a water soluble alcohol, then by one preparative, and lastly by one analytical molecular sieve filtration;

(c) a protein precipitation step with a water-soluble alcohol followed by one or two preparative and lastly by one analytical molecular sieve filtration.

The performance of the individual separation processes for the separation of the bulk of the accompanying foreign proteins from the AT and CT contained in the serum protein concentrate fraction in accordance with the process of the invention will now be described in specific detail.

Fractional elution of the serum protein concentrate fraction separates proteins largely independent of their molecular weight. The part of the foreign proteins that is soluble at higher ammonium sulfate concentrations than AT and CT, is separated from the concentrate. This separation method, therefore, is performed in form of a batch process in concurrence with the preparation of the serum protein concentrate fraction which has the advantage of being rapid and unstricted in capacity. If several separation steps are used in sequence, the fractional elution is, therefore, preferably carried out first.

Before the fractional elution, the protein mixture to be treated must be adjusted to an ammonium sulfate concentration sufficient for the precipitation of all the proteins. Such a suspension has an ammonium sulfate content of about 3.7 mol/l (at 0° to 8° C.) i.e. it is saturated to the extent of 90%. Adjustment to this ammonium sulfate content is done, for example, at the end of the separation of the entire AT- and CT-containing serum protein eluate from the cation-exchanger.

Concentration of proteins in the cation-exchanger eluate is carried out either directly by precipitation of proteins with ammonium sulfate. Or, if the eluate had been concentrated by a different process, such as ultrafiltration or lyophilization, ammonium sulfate is added to the concentrate to the given saturation.

For the fractional eluation of proteins, ammonium sulfate concentration of the serum protein concentrate fraction is adjusted to about 2.6 mol/l by addition of a protein-compatible liquid. Water or, preferably, a buffered salt solution can be used as such a liquid. Preferably, a pH between 4 to 8.5 and a temperature of approximately 0° to 8° C. is maintained. A special example of a suitable salt solution is a 0.001 mol/l sodium-potassium phosphate buffer containing 0.1 mol/l NaCl and having a pH of 6.3. When such an (ammonium sulfate-free) salt solution or water is used, about 0.4 volume parts per volume part of the serum protein concentrate fraction (as protein mud) is necessary to achieve the desired reduction in the ammonium sulfate concentration.

The ammonium sulfate concentration of the obtained protein suspension shall not be much lower than about 2.6 mol/l. Otherwise the AT and CT are dissolved as well. On the other hand, adjustment to an ammonium sulfate concentration much higher than about 2.6 mol/l is not advantageous, because then less foreign proteins are dissolved and thus, efficiency of the fractional elution decreases. To obtain a favourable solution equilibrium at the given ammonium sulfate concentration, the protein suspension is maintained at the given temperature and pH conditions for some time, preferably about 10 to 24 h with stirring. The remaining protein precipitate is then separated from the supernatant, for example by decantation or centrifugation.

Fractional elution in principle is the reverse process of fractional precipitation. For this reason this purification step, in principle, may be carried out as fractional precipitation. In such a case, the eluate of cation-exchange process is adjusted to an ammonium sulfate concentration of only about 2.6 mol/l instead of about 3.7 mol/l. The precipitating AT- CT-containing protein fraction is separated from the soluble supernatant. However, as is known from principles in protein fractionations, due to kinetics of precipitation equilibria, fractional elution has selective advantage over fractional precipitation as separation process. It may give higher yields than fractional precipitation. This also applies to this AT and CT fractionation process.

Separation of a part of accompanying foreign proteins from AT and CT by protein precipitation with a water-soluble alcohol makes use of the fact that under certain conditions a fraction of foreign proteins, but not AT and CT, is precipitated upon addition of a water-soluble alcohol to the protein solution. As for a fractional elution, this protein precipitation with alcohol is largely independent of the molecular weight of proteins. A large part of the accompanying proteins is separated from AT and CT. This separation step is preferably performed after the fractional elution process or instead of the latter purification step. In this way, for the following molecular sieve filtration the charge of the column used is considerably reduced.

Treatment with alcohol is carried out at a pH of about 3.5 to 5.5 and preferably at about 4.0, and at a maximum temperature of 8° C. and preferably about 5° C. Maintenance of given pH range is crucial. At lower pH, isolated proteins may be damaged. Higher pH may lower efficiency of the precipitation step. However, adjusting the pH only to the given range does not bring about precipitation of the foreign proteins.

The water-soluble alcohol is added in amounts of about 180 to 250, and preferably about 200 volume parts per 1000 parts of the protein solution. Smaller quantities of alcohol do not achieve complete precipitation. Higher alcohol concentrations do not induce better precipitating effects. They may, however, increase the risk for damage of mediators investigated by altering their confirmation. Special examples of suitable water-soluble alcohols are methanol, ethanol, propanol, and ethylene glycol. Ethanol is preferred as the water-soluble alcohol.

Protein precipitation with alcohol is performed with the (ammonium-sulfate-containing) muddy serum protein concentrate fraction obtained from the eluate of cation-exchange process or with the muddy protein residue obtained by the fractional elution step after their solution in a minimum volume of a protein compatible liquid. A special example of a suitable solution is 0.01 mol/l ammonium acetate solution containing 0.2 mol/l NaCl and having a pH of 5.0. The pH of the solution is then adjusted to the given range for example with glacial acetic acid after which the alcohol is added. For precipitation of foreign proteins, the solution is then maintained under the given conditions for some time, preferably with stirring. The precipitated foreign proteins are then separated from the supernatant which contain AT and CT dissolved, for example by decantation or centrifugation. The alcohol can then be removed, for example by dialysis, ultrafiltration, or lyophilization, from the supernatant protein solution. If a molecular sieve filtration step follows for further purification of AT and CT, the alcohol 46 daltons for $C_2H_5OH$) may be directly from the AT and CT (ca. 10,000 daltons) without the above-mentioned auxiliary methods.

Molecular sieve filtration achieves separation of proteins according to their molecular weights. Since the bulk of the foreign proteins have molecular weights greater than AT and CT, they can be separated off in this manner. A hydrophilic water-swelling molecular sieve is used for separation of the proteins by molecular weight. Examples of suitable molecular sieves are dextrans cross-linked with epichlorohydrin (Sephadex), agaroses cross-linked with acrylamide (Ultrogels), and three-dimensionally cross-linked acrylamides (Biogels), whose exclusion limits are higher than the separation limits used.

If several separation steps are used, the molecular sieve filtration is preferably carried out after a fractional elution and/or protein precipitation with water-soluble alcohol. In this way a major fraction of foreign proteins from all molecular weight ranges is already removed by the preceding separation steps. The proteins mass to be removed by the molecular sieve step is thus already considerably smaller. Depending on length-to-diameter ratio of the column used and particle diameter of the gel matrix, molecular sieve filtration is termed "preparative" or "analytical". A molecular sieve filtration is preparative when the chromatography is performed on columns with a length-to-diameter ratio of up to 10:1 and a charge of column of up to ⅓ of its capacity or use of total separation volume of the matrix. An analytical molecular sieve filtration means a length-to-diameter ratio greater than 10:1, and preferably about 50:1, and a maximum charge of column of up to 3% of its capacity.

In preparative molecular sieve chromatography, gel matrices with the largest possible particle size are used for maximum flow-through rates of mostly viscous protein solutions at reasonably low pressures. In analytical molecular sieve filtration the particle size ranges of the gel matrix selected are as small as possible, to obtain a maximum number of theoretical plates, a flow rate of the mobile phase equal to 2–4 cm/h combined with a pressure which is limited to technical and safety aspects. These parameters are dependent on the structure of the gel matrix and may vary from gel to gel.

If several preparative molecular sieve filtrations are performed in sequence, graduated separation limits can be selected. For example, a separation limit of 20,000 daltons can be used in a first filtration step and of 13,000 daltons in a second. This can be followed by an analytical molecular sieve filtration with upper and lower separation limits of 11,000 and 6000 daltons. The exclusion limit of the gel used in all cases must be higher than about 10,000 daltons to allow a volume distribution of AT (molecular weight about 9500) and CT (molecular weight about 8500) between the stationary gel matrix phase and the mobile aqueous buffer phase. Guinea-pig AT has a somewhat higher molecular weight of about 14,000 daltons. Therefore, in processing guinea-pig serum correspondent higher separation and exclusion limits must be used.

The "exclusion limit" is a hydrodynamic parameter of a dissolved particle corresponding to the pore size of the gel matrix. Particles with a greater hydrodynamic parameter cannot penetrate the gel matrix (volume distribution coefficient $K_D=0$). The "separation limit" refers to a hydrodynamic parameter which has been chosen for the separation of dissolved particles from others, with values between the volume distribution coefficients $K_D=0$ and $K_D=1$.

For molecular sieve filtration the proteins are applied to the molecular sieve after solution in a protein-compatible liquid. A special example of a suitable solvent is 0.01 mol/l sodium-potassium phosphate solution containing 0.3 mol/l NaCl and having a pH of 6.5. After the filtration AT- CT-containing fractions are collected. The dissolved proteins of the fractions are preferably concentrated by addition of ammonium sulfate to a concentration of 3.7 mol/l (90% saturation).

After separation of the precipitated proteins form the supernatant they are again dissolved in a protein-compatible liquid and, if necessary, subjected to a further purification step.

Between the above-described purification steps, if necessary, protein solutions can be separated from salts by dialysis or ultrafiltration, e.g. against sodium-potassium phosphate buffer. By selecting an appropriate mobile phase in the usual way, a modified molecular sieve filtration can also be used for this purpose. In the molecular sieve filtrations about 0.4 mol/l ammonium sulfate is preferably added to the protein solution. In contrast to higher concentrations of this salt, at this concentration ammonium sulfate exerts strong salting-in effect on proteins. Thus, proteins are better kept in solution during the molecular sieve filtration. Moreover, ammonium sulfate prevents growth of microorganisms and inhibits certain enzymes. Hence, it contributes to stabilization of the AT and CT, which is important when chromatography is performed at higher temperature (above about 20° C.) and under non-sterile conditions. To prevent oxidation, about 0.001 mol/l of cysteine is preferably added to protein solutions throughout.

The temperature and pH conditions during molecular sieve filtration are not particulary critical. If the native conformation of the proteins shall be preserved, a temperature range of about 0° to 8° C. and preferably about 0° to 4° C. is optional. The preferred pH range is between 6 and 9.

Use of above-mentioned separation processes according to the inventions, achieves separation of a major part of the accompanying foreign proteins from the mediators to be isolated, AT and CT, already prior to chromatography on hydroxyapatite. For example, according to one of the preferred embodiments, using fractional elution, two preparative and one analytical molecular sieve filtrations in sequence, a volume of protein solution of 100 liters of initial crude contact-activated serum (corresponding to about 35 liters of wet protein mass, or 7–8 kg of dry protein mass) can be reduced to less than about 100 to 200 ml before the first purification step (chromatography on hydroxyapatite). It is obvious that this makes possible for the first time preparing larger amounts of AT and CT. The quantity of protein to be chromatographed on hydroxyapatite is relatively small and already enriched in AT and CT. Hydroxyapatite columns with total absorption capacity for the intermediate product thus obtained ("crude leucotaxine preparation") from up to 200 liters of contact-activated crude serum can still be processed within the laboratory.

C. ISOLATION OF THE AT- AND CT-CONTAINING HIGHLY PURIFIED LEUCOTAXINE PREPARATION BY CHROMATOGRAPHY ON HYDROXYAPATITE

FURTHER PURIFICATION OF THE PREPARATION AND ITS SEPARATION INTO ANAPHYLATOXIN AND COCYTOTAXIN PROTEINS.

After performance of one or a combination of the separation processes described in section (B) the resulting protein solution, in which AT and CT are already enriched, is chromatographed on hydroxyapatite. This separates other foreign proteins and leads to an AT- and CT- containing highly purified leucotaxine preparation. The process is preferably carried out in the manner described by J. H. Wissler in Eur. J. Immunol. 2 (1972) p. 76, right-hand column.

Annomium sulfate and other salts, especially phosphate in the concentrated solution from the last proceding separation step (crude leukotaxine preparation) must be removed, preferably by dialysis, prior to application of protein solution to the hydroxyapatite. Apart from viscosity increase, however, only the phosphate concentration of the protein solution is critical for the chromatography on hydroxyapatite. The AT and CT are eluted by a sodium-potassium phosphate concentration gradient, which preferably is linear. The AT- and CT-containing fractions are collected and then concentrated, e.g. by addition of ammonium sulfate to a concentration of 3.7 mol/l and separation of the precipitated proteins by usual methods.

The leukotaxine preparation obtained by chromatography on hydroxyapatite consists of about 600 mg protein from 100 liters of serum. In general it contains about 60 to 70% of AT and CT. Thus, AT and CT constitute already a major portion in this purified product. However, if necessary, it may be further purified from residual contaminations by application of additional purification steps. Suitable further separation steps are rechromatography on hydroxyapatite, zone-precipitation chromatography, analytical molecular sieve filtration, or combinations of these steps.

The rechromatography on hydroxyapatite can be performed in the manner described by J. H. Wissler in Eur. J. Immunol. 1 (1972), p. 77, (right panel). Any foreign salts and ammonium sulphate possibly present are removed first from the leukotaxine preparation, preferably by dialysis. The resulting solution of the leukotaxine preparation then is applied to the hydroxyapatite column and eluted by a sodium potassium phosphate concentration gradient. The fraction containing the leukotaxine preparation are collected and concentrated in the usual manner.

In the zone-precipitation chromatography (cf. J. Porath, Nature, 196 (1962), p. 47–48), residual protein contaminations in the leukotaxine preparation are separated off by salt-out fractionation of the proteins with a salt concentration gradient. Temperature and pH, column dimensions, type of the salt, shape of the gradient, and column charge can be varied within relatively wide limits.

The temperature for zone-precipitation chromatography can be between 0° and 40° C. Preferably, a temperature range from about 0° to 10° C. is used, especially from about 4° to 6° C. The pH can be between 4 to 10; preferably, a pH range of 6 to 8 is used, especially a pH of about 7. The length-to-diameter ratio of the column used should be greater than about 10:1. A ratio of 30 to 100:1 and especially of about 50:1 is preferred. All salts having salting-out properties for proteins and being protein-compatible are suitable. Examples of such salts are sodium potassium phosphate, ammonium sulfate, and sodium sulfate. Ammonium sulfate is preferred.

The salt concentration gradient can have any desired shape within as long as the salting-out criteria of proteins provide protein separation. Linear concentration gradients are preferred, especially an ascending linear concentration gradient from 25 to 80% ammonium sulfate saturation. The maximum column charge is about 5% and preferably about 1% of total column volume.

Analytical molecular sieve filtration for further purification of the leukotaxine preparation can be performed in the same manner as described for separation of foreign proteins prior to chromatography on hydroxyapatite. The same molecular sieves, columns and performance conditions can be used.

A considerable separation of contaminating foreign proteins still present in the leukotaxine preparation (in addition to AT and CT) can already be achieved by one of the above-mentioned, additional purification steps. For example, by rechromatography on hydroxyapatite, a leukotaxine preparation is obtained in which AT and CT make up to about 91% of total protein present. Zone-prcipitation chromatography increases the AT and CT fraction of the leucotaxine preparation to about 94%, and a single analytical molecular sieve filtration increases it to about 95%. If only one additional purification step is performed, zone-precipitation chromatography is preferred.

The basic principle of separation of proteins by zone-precipitation chromatography are different, structure-related reversible solubility characteristics of proteins. They belong to the most sensitive molecular separation criteria and are often used for demonstration of molecular homogeneity of a protein. This explains preference of zone-precipitation chromatography over the various types of rechromatography methods, in which purification effects are based on optimum approximation to ideal equilibria in non-ideal polyelectrolyte systems.

The therapeutic use, the leukotaxine preparation is preferably almost completely freed from contaminating foreign proteins by combination of at least two of the mentioned purification steps. Especially, a sequence of steps is preferred, in which the leukotaxine preparation obtained by chromatography on hydroxyapatite is first rechromatographed on hydroxyapatite, then subjected to a zone-precipitation chromatography, and finally to an analytical molecular sieve filtration. In another preferred embodiment rechromatography on hydroxyapatite can also be performed after the zone-precipitation chromatography. In these preferred embodiments a leukotaxine preparation is obtained in which total protein content consists of up to more than 99% of AT and CT.

The AT and CT-containing leukotaxine preparation obtained by chromatography on hydroxyapatite can be separated by chromatographic methods into the individual components investigated, AT and CT, either directly after the first chromatography on hydroxyapatite, or after one of the above-mentioned additional purification steps. If necessary, AT and CT can then be purified individually from small amounts of accompanying foreign proteins. This is achieved with the purificationn techniques above-mentioned for purification of the leukotaxine preparation. Thus, AT and CT can be obtained in crystalline form.

The resolution of the leukotaxine preparation into AT and CT is preferably carried out by modification of the process described by J. H. Wissler in Eur. J. Immunol. 2 (1972), p. 78, using cascade and recycling molecular sieve filtration. Separation into the two proteins occurs in the first of the two separation steps. The second step serves for removal of small amounts of the respective other protein from the AT and CT respectively.

The cascade and recycling molecular sieve filtration can be performed under the conditions described above for the analytical molecular sieve filtration. The same molecular sieves and the same chromatography conditions can be used. Sephadex G50 is preferred, with a column of a minimum length-to-diameter ratio of about 50:1 and a maximum charge up to about 3% of the column capacity. The solvents neecessary for elution preferably are the same as used for analytical molecular sieve filtration.

In cascade molecular sieve filtration, at a certain separation limit, the eluate is applied to a column cascade composed, for example, of two columns of the same specifications. Through increased column length, the leukotaxine preparation is separated into two main fractions of a molecular weight of 9500 daltons (AT) and 8500 daltons (CT).

After separation, both fractions (AT and CT) are individually concentrated e.g. by salting-out precipitation with ammonium sulfate. For separation of the residual component of each of the other protein, At and CT can be subjected separately to a further cascade or recycling molecular sieve filtration. The latter differs from the former in that the eluate is not passed, at the given separation limit, through a cascade of further columns but is reapplied to the same column. The column length for the proteins is thus increased. The small amounts of each of the protein isolated from the bulk of the other protein then can be added to the main fraction obtained in the first cascade molecular sieve filtration.

As already mentioned, the separation of the leukotaxine preparation into its protein components can be carried out directly after having been yielded in the first chromatography on hydroxyapatite or following one of the described additional purification steps. If separation into AT and CT is intended, it is preferably performed following the first chromatography on hydroxyapatite. Effective purification of the AT and CT proteins obtained is achieved by individual sequences consisting of rechromatography on hydroxyapatite, zone-precipitation chromatography, and/or analytical molecular sieve filtration.

As already stated, temperature and pH conditions are not particularly critical in most of the steps of the process in accordance with the invention. However, if the leukotaxine protein preparation or the AT and CT proteins have to be obtained in their native conformation, the separation and purification steps are carried out under almost physiological pH and salt conditions, and preferably at low temperatures with a maximum of about 10° C. and preferably 6° C. An essential advantage of the process in accordance with the inventions is that these conditions can be easily verified.

The resulting leukotaxine protein preparation or the separated AT and CT proteins can be stored in a physiological, buffered salt solution, e.g. in 0.0015 mol/l potassium phosphate solution containing 0.15 mol/l (0.9 w/v %) NaCl, 0.001 mol/l cysteine and having a pH of 7.4. After usual sterilization by filtration (pore size 0.2 82 m), the protein preparation remains native and biologically active at room temperature (for at least 200 h) or frozen at −25° C. (for at least 6 years). This stability of the protein preparations can be considered as one of the criteria of molecular homogeneity. A safe storage form at temperatures between −20° and =50° C. is the crystalline state of the proteins in the form of a crystal suspension, prepared according to the method described by J. H. Wissler, op. cit. In this form it is also protected against infection and degradation by microorganisms.

The invention will now be given in detail by examples describing the isolation of the leucotaxine preparation and of the individual AT and CT proteins starting from porcine blood. However, in terms of the species used the invention is not restricted to this form of embodiments.

EXAMPLE A

Production of Anaphylatoxin and Cocytotaxin in serum

Separation of an AT- andCT-containing serum protein concentrate fraction from other serum constituents.

The production of AT and CT in the serum and the separation of a major serum protein concentrate fraction from the other serum constituents are explained.

300 liters of porcine blood are coagulated without additives at room temperature. The supernatant serum is separated from the clot by centrifugation. The clear serum is then mixed and contact-activated immediately with 5 mg dextran per ml serum or with 100 mg bakers' yeast per ml serum and incubated by stirring in a water-bath for 1 h at 37° C. Then, the mixture is cooled at 4° C. and dextran or yeast is removed by centrifugation. The presence of anaphylatoxin and of cocytotaxine in the 120 liters of contact-activated serum obtained, which contains about 9.2 k of protein, is demonstrated by activity assays (chemotaxis of neutrophil leukocytes and anaphylatoxin activity).

Unless otherwise specified, the following purification techniques are then performed in the presence of 0.001 mol/l cysteine at a temperature of 0° to 8° C.:

120 liters of contact-activated serum are adjusted to pH 4.5 with 5 mol/l acetic acid and mixed with 240 liters of 0.001mol/l potassium phosphate-acetate buffer containing 0.2 mol/l NaCl and having a pH of 4.5. Then, 3 volume parts of the protein solution obtained are mixed by stirring in 1 volume part of a swollen, regenerated cation-exchanger ($Na^+$as mobile exchangeable counter-ion) coupled to a dextran matrix cross-linked by epichlorohydrin (CM-Sephadex C-50). The ion-exchanger used has been pretreated for at least 1 day with porcine serum for surface inactivation, regenerated prior to use, and equilibrated with the phosphate-acetate buffer of pH 4.5.

The resulting mixture is stirred for about 24 h. The ion-exchange gel is then settled and separated from the supernatant by filtration on a Büchner funnel. The gel is washed with three 120-liter portions of 0.001 mol/l potassium hydrogen phosphate-acetate buffer containing 0.2 mol/l NaCl and having a pH of 4,5, until the extinction of the filtrate at 280 nm is E=1.0.

For elution of the absorbed proteins, the charged ion-exchange gel is suspended three times in the same volume part of 0.5 mol/l potassium phosphate buffer at pH 6.5. The ion-exchange gel is separated from the solution each time by centrifugation or filtration. The protein solutions obtained are combined (360 liters).

The combined eluates of the cation-exchange gel are adjusted to a concentration of ammonium sulfate of 90% saturation by addition of 630 g of ammonium sulfate per liter eluate protein solution. During addition, the pH of the protein solution is checked continuously and maintained between 6.5 and 7.0 by addition of 2 mol/l ammonia. AT and CT precipitate of the solution together with the majority of serum proteins. The protein precipitate is separated from the almost protein-free supernatant salt solution by centrifugation for 1 h at 10,000×g. 49 liters of ammonium sulfate-containing protein mud are obtained, containing about 3.5 kg of protein (serum protein concentrate fraction).

EXAMPLE B

Crude purification of AT and CT: Separation of the bulk of the accompanying foreign proteins from the AT and CT Preparation of a crude AT- and CT-containing leukotaxine preparation.

Example B1: Crude separation of AT and CT by fractional elution of contaminating foreign proteins For fractional elution, 49 liters of the serum protein-concentrate fraction obtained as a mud as described above under example A, having an ammonium sulfate concentration of about 3.7 mol/l (90% saturation) are treated with 0.001 mol/l sodium-potassium phosphate buffer containing 0.1 mol/l NaCl, 0.001 mol/l cysteine and having a pH of 6.3 in quantities of 0.4 volume parts per volume part of serum protein concentrate fraction mud under stirring for about 24 h. Then, the residual insoluble protein precipitate which contains almost all AT and CT, is separated from the supernatant eluate by centrifugation at 10,000 ×g. About 70% (2.7 kg protein) of the starting serum protein concentrate fraction remain in the form of a mud (volume: about 14 liters). For removal of ammonium sulfate, this protein mud containing AT and CT and representing a crude leukotaxine preparation is dialysed at a membrane with an exclusion limit of 1000 daltons against 0.001 mol/l sodium- potassium phosphate solution containing 0.1 mol/l NaCl, 0.001 mol/1 cysteine and having a pH of 7.4. 40 liters of ammonium sulfate-free protein solution are obtained and applied to a hydroxyapatite column according to Example C.

Example B2:

Crude separation of AT and CT byfractional precipitation of contaminating foreign proteins For fractional precipitation, 49 liters of the serum protein concentrate fraction obtained as a mud as described above under Example A, are dissolved in a minimum volume of 0.01 mol/l ammonium acetate buffer containing 0.2 mol/l NaCl and having a pH of 5.0. One volume part of the resulting protein solution is adjusted to pH 4.0 with glacial acetic acid under stirring and mixed with 0.2 volume parts of 96% ethanol at a temperature of 0° C. During addition of ethanol, the temperature and the pH are maintained constant. The mixture is stirred for 1 h at 0° C. 70% (2.45 kg) of foreign proteins present in solution are precipitated and separated from AT- and CT-containing supernatant solution by centrifugation for 1 h at at least 16,000×g. The separated precipitate of foreign proteins (10 liters) is washed four times with an equal volume of 0.01 mol/l ammonium acetate buffer containing 0.2 mol/l NaCl, 200 ml ethanol per liter buffer and having a pH of 4.0, at a temperature of 0° C. The washings are combined with the AT- and CT-containing supernatant solution from the centrifugation and the mixture is adjusted to pH 5.0 using 2 mol/l ammonia. Then, the ethanol is separated off by lyophilization, molecular sieve filtration, or dialysis (exclusion limit 1000 daltons) against the ammonium acetate buffer. If dialysis or molecular sieve filtration have been used, the proteins are precipitated in the alcohol-free solution obtained by the addition of ammonium sulfate (90% saturation) and separated from the almost protein-free supernatant salt solution by centrifugation at 10,000×g. The protein residue obtained by lyophilization or precipitation (1.05 kg protein) which contains AT and CT and represents a crude leukotaxine preparation, is freed from the ammonium sulfate and other salts by dialysis as given in Example B1. The protein solution obtained can be applied onto the hydroxyapatite column as an ammonium sulfate-free solution (volume 16 liter) as described in Example C2.

Example B3: Crude separation of AT and CT from contaminating foreign proteins by preparative molecular sieve filtration For preparative molecular sieve filtration 1 volume part (49 liters) of serum protein precipitate fraction obtained as a mud as described above under Example A, are dissolved in 2 volume parts of 0.03 mol/l sodium-potassium phosphate solution containing 0.3 mol/l NaCl, 0.001 mol/l cysteine and having a pH of 6.7. The solution is centrifuged for 30 min at 4° C. and 10,000×g. for removal of small amounts of insoluble particles. Then, the clear solution (147 liters) is subjected to a preparative molecular sieve filtration. Therefore, it is applied to a column packed with a molecular sieve matrix of dextran cross-linked with epichlorohydrin (Sephadex G-50; particle size 50 to 150 μm). The column has a 10-fold volume of the protein solution volume and a length-to-diameter ratio of 10:1. The column is eluted with ascending flow (rate 3 cm/h) with 0.03 mol/l sodium-potassium phosphate buffer containing 0.3 mol/l NaCl, 0.001 mol/l cysteine, 0.4 mol/l ammonium sulfate and having a pH of 6.7. The amount of buffer used for elution corresponds to the total column volume. The eluate is divided into two fractions with a separation limit of 20,000. The fraction with molecular weight larger than 20,000 daltons contains 85% of the initial foreign protein mass. The AT- and CT-containing fraction (0.5 kg of protein) with molecular weights smaller than 20,000 daltons is collected and constitutes the crude leukotaxine preparation. The proteins of this fraction are concentrated as given in Example B2 by precipitation with ammonium sulfate and, then, separation of ammonium sulfate by dialysis. The resulting solution which still contains 15% of the original protein mass (7.5 liters), has a volume of 22.5 liters and can be applied to the hydroxyapatite column as will be described in Example C.

Example B4: Crude separation of AT and CT from contaminating foreign proteins by a sequence of fractional elution and preparative molecular sieve chromatography 49 liters of the serum protein concentrate fraction obtained as a mud as described above in Example A, are fractionally eluted as given in Example B1. The resulting 14 liters of protein mud containing AT and CT, are dissolved in sodium-potassium phosphate buffer as described in Example B3. The resulting solution is processed for chromatography on Sephadex G-50 as described in Example B3. The fraction with molecular weights smaller than 20,000 daltons is collected, concentrated with ammonium sulfate, and finally dialysed. 6.0 liters of ammonium-sulfate-free protein solution is obtained, with a protein content of 0.4 kg, containing AT and CT and constituting a crude leukotaxine preparation. This solution can be further processed as given in Example C.

Example B5: Crude separation of AT and CT from contaminating foreign proteins by a sequence of fractional precipitation and preparative molecular sieve chromatography 49 liters of the serum protein concentrate fraction obtained as a mud as given in Example A are treated with ethanol for fractional precipitation of foreign proteins as given in Example B2. The protein residue obtained after removal of ethanol and concentration of proteins from the supernatant solution (1.05 kg of protein) then is dissolved and chromatographed on a molecular sieve as given in Example B3. 2.3 liters of ammonium-sulfate-free protein solution are obtained, with a protein content of 160 g, containing AT and CT and representing a crude leukotaxine preparation.

Example B6: Crude separation of AT and UT from contaminating foreign proteins by a sequence of fractional elution, two preparative and one analytical molecular sieve filtrations 49 liters of the serum protein concentrate fraction obtained as mud as described above in Example A are fractionally eluted and then subjected to a preparative molecular sieve filtration as described in Example B4.

After concentration of proteins in the AT- and CT-containing fraction with a molecular weight smaller than 20,000 daltons by salting-out precipitation with ammonium sulfate, the obtained AT- and CT-containing protein precipitate is dissolved in 0.03 mol/l sodium-potassium phosphate buffer containing 0.3 mol/l NaCl, 0.001 mol/l cysteine and having a pH of 6.7. 1.5 volume parts of buffer per volume part of protein precipitate mud is used. A small amount of residual insoluble material is centrifuged off. For preparative molecular sieve rechromatography the solution is applied to a column packed with a molecular-sieve matrix of dextran cross-linked with epichlorohydrin (Sephdex G-50; particle size 50 to 150 μm). The column has a 10 fold volume of the protein solution and a length-to-diameter ratio of 10:1. The column is eluted in ascending mode at 3 cm/h with 0.03 mol/l sodium-potassium phosphate buffer containing 0.3 mol/l NaCl, 0.001 mol/l cysteine, 0.4 mol/l ammonium sulfate and having a pH of 6.7. The resulting eluate is divided into three fractions with separation limits larger than 20,000, smaller than 13,000 daltons and an intermediate fraction. The AT- and CT-containing protein fraction with a molecular weight range smaller than 13,000 daltons contains 130 g of protein and represents a crude leukotaxine preparation. It is adjusted to an ammonium sulfate concentration of 3.7 mol/l for salting-out precipitation of proteins. The protein-precipitate is separated from the supernatant by centrifugation.

The AT- and CT-containing protein precipitate obtained is dissolved in 1,5 volume parts of the buffer solution as described above in the preceding molecular sieve filtration with ammonium sulfate omitted. The solution is centrifuged for 1 h at 10,000×g to remove a small quantity of insoluble residue. For analytical molecular sieve filtration, the obtained clear solution is applied to a column packed with a molecular-sieve matrix of dextran cross-linked with epichlorohydrin (Sephadex G-50) with a particle size of 20 to 80 μm. The column used has a 50-fold volume of the protein solution and a length-to-diameter ratio of 50:1. For elution in ascending mode (3 cm/h) a 0,03 mol/l sodium-potassium phosphate buffer containing 0.3 mol/l NaCl, 0.001 mol/l cysteine, and 0.4 mol/l of ammonium sulfate with a pH of 6.7 is used. The resulting eluate is divided into several fractions, which chemotactic properties for neutrophil leukocytes and anaphylatoxin activity are tested. An intermediate fraction with a molecular weight range of 11,000 to 6000 daltons, containing essentially all AT and CT and representing a crude leukotaxine preparation is separated off. This fraction is adjusted to an ammonium sulfate concentration of 3.7 mol/l for salting-out precipitation of proteins. The precipitated proteins are removed from the supernatant by centrifugation. They can be dissolved as usually described in the preceding steps or, preferentially, as given in Example C1, and a small amount of insoluble material is removed by centrifugation. Yield: 200 ml of clear concentrated protein solution with a protein content of 0.9 g.

FIGS. 1 to 3 show the course of the separation of the crude AT- and CT-containing leukotaxine preparation from the accompanying contaminating foreign proteins by a sequence of two preparative and one analytical molecular seive filtration in form of chromatograms.

Example B7: Crude separation of AT and CT from contaminating foreign proteins by a sequence of fractional elution, fractional precipitation, one preparative and one analytical molecular seive filtration processes 49 liters of the serum protein concentrate fraction obtained as a mud as described in Example A, are treated sequentially for fractional elution (Example B1; result: 14 liter of protein mud) and for fractional precipitation of foreign proteins (Example B2). The protein residue obtained (1.05 kg of protein) after removal of ethanol and concentration of soluble proteins of the supernatant solution is subjected to the second preparative molecular sieve filtration and, then, sequentially to an analytical molecular sieve filtration, both described in Example B6. The same result for the crude, AT- and CT-containing leukotaxine preparation as in Example B6 is obtained.

Example B8: Crude separation of AT and CT from contaminating foreign proteins by a sequence of fractional precipitation, two preparative and one analytical molecular sieve filtration processes 49 liters of the serum protein concentrate fraction obtained as a mud as described in Example A, are first treated sequentially with ethanol for fractional precipitation of foreign proteins and subjected to a preparative molecular sieve filtration as described in Example B5. The protein residue obtained after concentration (160 g of protein) is dissolved as described and then subjected as given in Example B6 to a sequence of the second preparative and to the analytical molecular sieve filtration. The same result for the crude, AT- and CT-containing leukotaxine preparation as in Example B6 is obtained.

EXAMPLE C. Isolation of the AT- and CT-containing purified leukotaxine preparation by chromatography on hydroxyapatite. Further processing to a highly purified leukotaxine preparation into separated, individual AT and CT proteins and to their molecular homogeneity Example C1: Chromatography of the AT- and CT-containing crude leukotaxine preparation B6 on hydroxyapatite The AT- and CT-containing crude leukotaxine protein precipitate obtained in Example B6 is dissolved in a minimum volume of 0.0015 mol/l sodium-potassium phosphate buffer containing 0.15 mol/l NaCl and 0.001 mol/l cysteine. A small amount of residual insoluble material is discarded after separation by centrifugation (10,000×g, 1 h, 4° C.). The clear solution is dialysed against 0.001 mol/l sodium-potassium phosphate buffer containing 0.1 mol/l NaCl, 0.001 mol/l cysteine and having a pH of 7.4, ultrafiltered, or desalted by molecular sieve filtration (exclusion limit: 1000 daltons) until no sulfate is any more detectable in the solution. A small fraction of insoluble proteins is then removed by centrifugation for 1 h at 10,000 g and 4° C.

The clear AT- and CT-containing leukotaxine protein solution obtained (200 ml; protein content: 9.0 g) is applied to a column packed with hydroxyapatite. The column has a length-to-diameter ratio of 10:1 and 3-fold volume of the protein solution volume to be applied (45 mg protein/ml). Prior to the application of the leukotaxine preparation, the column is first equilibrated with a 5-fold volume of 0.001 mol/l sodium-potassium phosphate buffer containing 0.1 mol/l NaCl, 0.001 mol/l cysteine and having a pH of 7.4 (flow rate 3 cm/h).

The negatively adsorbing proteins are washed out by elution with the buffer solution used to equilibrate the column. Then, elution of the AT- and CT-containing leukotaxine fraction is performed within 4 days with a linear phosphate concentration gradient of 0.001 mol/l of sodium-potassium phosphate buffer of pH 7.4, having the given constant NaCl and cysteine concentrations. The elution gradient is measured by conductivity. A usual step (salting-out precipitation or ultrafiltration) for concentration of active fractions is applied. A suitable buffer for dissolving the protein concentrate is 0.001 mol/l sodium-potassium phosphate buffer containing 0.001 mol/l cysteine and having a pH of 7.2. Thus, it is possible to adjust to any other salt concentration by addition of a small volume of a concentrated salt concentration by addition of a small volume of a concentrated salt solution For example, if required, addition of 0.05 volume parts of a 2 mol/l NaCl solution of pH 7.2 results a phosphate buffered protein solution with 0.1 mol/l NaCl. A protein solution volume of 14 ml is obtained, cotaining 650 mg of the product, which represents a leukotaxine preparation with an AT and CT content of about 70% of total protein.

The isolation of the AT- and CT-containing purified leukotaxine preparation by chromatography on hydroxyapatite as described in Example C1 is shown in the chromatogram of FIG. 4.

Example C2: Chormatography of the AT- and CT-containing crude leukotaxine preparation B2 on hydroxyapatite Example C1 is repeated with the AT- and CT-containing crude leukotaxine protein precipitate obtained as described in Example B2. According to the description given in Example B2 after dialysis and removal of a small fraction of insoluble proteins, 16 liters of clear leukotaxine protein solution are obtained and applied to a column packed with hydroxyapatite with characteristics as given in Example C1 (volume 3×16 liters, length-to-diameter ratio 10:1); i.e. with a diameter of 18 cm and a length of 180 cm. After elution, about 700 mg of the purified leukotaxine-containing product is obtained, which has an AT and CT portion of about 65% of total protein content.

Example C3: Further process of the purified product C1 to an AT- and CT-containing highly purified leukotaxine preparation by zone-precipitation chromatography.

The AT- and CT-containing leukotaxine preparation obtained as given in Example C1 is dissolved in 0.1 mol/l sodium-potassium phosphate solution containing 0.1 mol/l NaCl, 0.001 mol/l cysteine, 1 mol/l of ammonium sulfate and having a pH of 7.4 to result a protein concentration of about 45 mg/ml. At a temperature 4° C. the solution obtained (14 ml) is applied to a column packed with a molecular-sieve matrix of dextran cross-linked with epichlorohydrin (Sephadex G-50). The matrix is equilibrated with an ascending linear ammonium sulfate concentration gradient of 1.0 to 3.2 mol/l (25 to 80% saturation) of ammonium sulfate. The gradient corresponds to a 2% increase in the ammonium sulfate concentration per cm of column length. The gradient ranges over half of the column length. Thus, the other half of column length is equilibrated with the buffer containing a constant concentration of 3.2 mol/l ammonium sulfate. The length-to-diameter ratio of the column is 50:1, and the column volume has 100 fold volume of the solution applied. The flow rate is 2 cm/h.

Protein elution from the column is done with the above-described sodium-potassium phosphate buffer containing 1 mol/l of ammonium sulfate. The active fractions are collected and the proteins are concentrated in the usual manner (salting-out precipitation or ultrafiltration). For dissolving of the protein concentrate obtained, a buffer as given in Example C1 is preferably used (0.001 mol/l sodium-potassium phosphate buffer containing 0.001 mol/l cysteine and having a pH of 7.2). 460 mg (10 ml) of purified AT- and CT-containing leukotaxine preparation is obtained, consisting of about 94% of AT and CT of total protein content.

Example C4: Further processing of purified product C1 to an AT- and CT-containing, highly purified leukotaxine preparation by a sequence of rechromatography on hydroxyapatite, zone-precipitation and analytical molecular sieve chromatography.

The AT- and CT-containing, purified leukotaxine preparation obtained as given in Example C1 (650 mg; about 14 ml with 45 mg protein/ml) is dialysed against 0.001 mol/l sodium-potassium phosphate buffer containing 0.001 mol/l cysteine and having a pH of 7.2, ultrafiltrated, or desalted by molecular sieve filtration (exclusion limit 1000 daltons). Then, a small fraction of insoluble proteins is removed by centrifugation for 30 min at 32,000×g and 4° C. The clear solution obtained is rechromatographed in the above buffer system on a column packed with hydroxyapatite which is equilibrated with the given buffer system. The column has a length-to-diameter ratio of 20:1 and at least a 5-fold volume of protein solution applied. The elution is carried out with a phosphate concentration gradient as given in Example C1. After concentration of active fractions pooled, 410 mg of highly purified leukotaxine preparation are obtained. About 91% of total protein content consist of AT and CT.

This highly purified leukotaxine preparation obtained above is now subjected to a zone-precipitation chromatography as described in Example C3. After concentration of active fractions, 395 mg (10 ml) of further highly purified AT-and CT-containing leukotaxine preparation are obtained. It now consists of about 96% of AT and CT.

Finally, this highly purified, AT- and CT-containing leukotaxine preparation obtained as given by a sequence of chromatography and rechromatography on hydroxyapatite and zone-precipitation chromatography is subjected to an analytical molecular sieve filtration. The leukotaxine protein concentrate is dissolved in 0.003 mol/l sodium-potassium phosphate buffer containing 0.3 mol/l NaCl, 0.001 mol/l cysteine and having a pH of 7.4, to result an total maximum volume of 10 ml with a protein concentration of about 35 to 40 mg/ml. The clear solution obtained is applied to a column packed with Sephadex G-50 having a particle size of 20 to 80 μm. The column used has at least a 50-fold volume of the protein solution and a length-to-diameter ratio of at least 50:1. For elution, a 0.03 mol/l sodium-potassium phosphate buffer containing 0.3 mol/l NaCl, 0.001 mol/l cysteine, 0.4 mol/l ammonium sulfate and having a pH of 7.4 is used (flow rate: 3 cm/h). After the usual concentration step for the active fractions, 370 mg (10 ml) of a highly purified leukotaxine preparation are obtained. It consists of more than 99% of AT and CT (total yield: about 12%).

After desalting by dialysis, ultrafiltration, or molecular sieve filtration with an exclusion limit of 1000 daltons against physiological, buffered saline solution (e.g. 0.0015 mol/l sodium-potassium phosphate buffer containing 0.15 mol/l (0.9%) NaCl, 0.001 mol/l cysteine and having a pH of 7.4), and after sterilization by filtration (pore size 0.2 μm), the highly purified AT-CT-containing leukotaxine preparation can be used for biological, physiological, pharmacological, and biochemical purposes.

EXAMPLE C5: Further Processing of the purified AT- and CT-containing leukotaxine preparation C1 into separated, individual AT and CT-proteins and to their molecular homogeneity The purified, AT- and CT-containing leukotaxine preparation obtained as described in Example C1 (650 mg; about 14 ml with 45 mg protein/ml) is transferred to a 0.003 mol/l sodium-potassium phosphate buffer containing 0.3 mol/l NaCl, 0.001 mol/l cysteine and having a pH of 7.4, as given in Example C1 (final volume: 16 ml). After centrifugation at 10,000 ×g, 4°, for 30 min, a small quantity of insoluble materials is removed. The clear solution obtained is applied to a column packed with Sephadex G-50 with a particle size of 20 to 80 μm at a temperature of 4° C. The column has a 50-fold volume of the protein solution and a length-to-diameter ratio of 50:1. Elution is performed with a 0.03 mol/l sodium-potassium phosphate buffer containing 0.3 mol/l NaCl, 0.001 mol/l cysteine, 0.4 mol/l ammonium sulfate and having a pH of 7.4.

At a separation limit of 11,000 daltons, the eluate is introduced onto a threefold analytical molecular-sieve filtration cascade composed of two columns of the same specifications. Two main fractions with average molecular weights of 9500 daltons (130 mg AT) and 8500 daltons (325 mg CT) are obtained.

The two separated, individual protein fractions (AT and CT) obtained are concentrated as usual by the addition of ammonium sulfate. The precipitated proteins are then dissolved separately in the above-described buffer. The obtained clear solutions are individually subjected to analytical molecular sieve recycling chromatography under the conditions given above for cascade chromatography.

The eluates are recycled three times at a separation limit of 10,000 daltons (for AT) and 9000 daltons (for CT) as specified for cascade chromatography.

AT-recycling chromatography yields 113 mg of product with a molecular weight of 9500 daltons (AT) and 10 mg with a molecular weight of 8500 daltons (CT). CT recycling chromatography delivers 312 mg of product with a molecular weight of 8500 daltons (CT) and 15 mg with a molecular weight of 9500 daltons (AT). Each of the small residual amount of the proteins is combined with its main quantity. The two proteins are then as usually individually concentrated (by ultrafiltration or salting-out precipitation with ammonium sulfate) and the protein precipitates dissolved as described in Example C1.

Then, the two protein fractions (AT and CT) are subjected separately to a final purification consisting of three steps as described in Example C4. The same conditions are used as for the joint purification of AT and CT within the leukotaxine preparation. The sequence of the three steps consists of one rechromatography on hydroxyapatite, one zone-precipitation chromatography, and one analytical molecular sieve chromatography for each of the two proteins (AT and CT).

For anaphylatoxin, 100 mg of the AT-protein are obtained (about 10% total yield). The preparation consists of more than 99% of AT. Protein contaminations cannot be detected on the basis of electrophoretic, chromatographic, immuno-analytical and solubility criteria. The AT preparation can thus be considered as molecularly homogeneous.

For cocytotaxine, 250 mg of the CT-protein are obtained (about 11% total yield). The preparation consists of more than 99% of cocytotaxine. Protein contaminations cannot be detected on the basis of electrophoretic, chromatographic, immunoanalytical and solubility criteria. The CT preparation can as well be considered as molecularly homogeneous.

The separation of the AT- and CT-containing leukotaxine preparation into the proteins AT and CT and their further individual purification to molecular homogeneity as described in Example C5 are shown in the chromatograms presented in FIGS. 5 to 13.

As already mentioned, the absolute properties and quantities yielded and the ratio of the proteins AT and CT obtained in the process may vary somewhat with the origin and contact-activation method of blood and the animal species used.

Thus, for example, as is known classical anaphylatoxin derived from normal human serum has only a very low spasmogenic activity on smooth muscles, when compared to classical AT derived from normal porcine, rat or guinea pig serum. However, the combination of AT and CT has a high chemotactic activity for neutrophil leucocytes which is comparable to the protein combination derived from normal porcine, rat and guinea pig blood. The processes for obtaining AT and CT, however, are not restricted for use with normal, contact-activated mammalian serum. If protease inhibitors (like 6-amino caproic acid, di-isopropyl-fluoro-phosphate, etc.) are added for special purposes to the sera, process examples B2, B3, B5, B8 are especially suitable for an initial, crude removal of contaminating foreign proteins, followed by a suitable selection of process examples C for obtaining highly purified proteins. Due to the known action of some of such protease inhibitors on serum encyme systems, and depending on conditions of contact-activation of the sera, modified, natural protein analogues of AT and CT formed as intermediates in sequences of steps of the AT- and CT-formation process can as well be isolated as fractions in the process of the invention.

After transfer of the two individual proteins AT and CT into a physiological buffered saline solution and after their sterilization as described in Example C4, the two individual proteins can be used for appropriate biochemical, physiological, pharmacological, or biological purposes. Or, each can be crystallized according to the known methods (J. H. Wissler, op. cit.).

What is claimed is:

1. In a process for producing and obtaining an anaphylatoxin- and cocytotaxin-containing leucotaxine preparation in biologically active form from contact-activated mammalian serum, the process including separating proteins from other serum constituents to obtain a serum protein concentrate fraction, separating a part of accompanying foreign blood proteins from anaphylatoxin and cocytotaxin present in said protein concentrate fraction, and isolating the leucotaxine preparation by chromatography on hydroxyapatite, wherein the improvement comprises separating prior to chromatography on hydroxyapatite, a major fraction of accompanying foreign blood constituents from said serum protein concentrate fraction by fractional elution and then filtering the residual protein precipitate containing anaphylatoxin and cocytotaxin by molecular sieve filtration.

2. A process according to claim 1 wherein the serum protein concentrate fraction is first fractionally eluted and the residual anaphylatoxin- and cocytotaxin-containing precipitate is then subjected twice to preparative molecular sieve filtration and once to analytical molecular sieve filtration in water or in a protein-compatible liquid.

3. A process according to claim 2 wherein the first preparative molecular sieve filtration is replaced by precipitation of foreign accompanying proteins with a water-soluble alcohol.

4. A process according to claims 1, 2 or 3 wherein for fractional elution, the serum protein concentrate fraction is adjusted to an ammonium sulfate concentration of approximately 2.6 mol/l with a protein-compatible liquid.

5. A process according to claim 4 wherein said protein-compatible liquid is, 0.001 mol/l sodium potassium phosphate buffer containing about 0.1 mol/l NaCl and having a pH of approximately 6.3.

6. A process according to claims 2 or 3 wherein the first preparative molecular sieve filtration is carried out at a temperature of 0° to 8° C. and a pH of 6 to 8 on a hydrophilic, water-swelling molecular sieve having a separation limit of 20,000 daltons.

7. A process according to claims 2 or 3 wherein the second preparative molecular sieve filtration is carried out at a temperature of 0° to 8° C. and a pH of 6 to 8 on a hydrophilic, water-swelling molecular sieve having a separation limit of 13,000 daltons.

8. A process according to claims 2 or 3 wherein the analytical molecular sieve filtration is carried out at a temperature of 0° to 8° C. and a pH of 6 to 8 on a hydrophilic water-swelling molecular sieve with separation limits of 11,000 and 6000 daltons.

9. A process according to claim 6, wherein the molecular sieve filtration is carried out in the presence of ammonium sulfate at a concentration of up to about 0.6 mol/l.

10. A process according to claim 7, wherein the molecular sieve filtration is carried out in the presence of ammonium sulfate at a concentration of up to about 0.6 mol/l.

11. A process according to claim 8, wherein the molecular sieve filtration is carried out in the presence of ammonium sulfate at a concentration of up to about 0.6 mol/l.

12. A process according to claim 6, wherein the molecular sieve filtration is carried out in the presence of cysteine at a concentration of up to about 0.001 mol/l.

13. A process according to claim 7, wherein the molecular sieve filtration is carried out in the presence of cysteine at a concentration of up to about 0.001 mol/l.

14. A process according to claim 8, wherein the molecular sieve filtration is carried out in the presence of cysteine at a concentration of up to about 0.001 mol/l.

15. In a process for producing and obtaining anaphylatoxin and cocytotaxin proteins in molecularly homogeneous, biologically active form from contact-activated mammalian serum, the process comprising separating the proteins from other serum constituents to obtain a serum protein concentrate fraction, separating a part of accompanying foreign blood proteins from anaphylatoxin and cocytotaxin present in the said protein concentrate fraction, isolating the leucotaxine preparation by chromatography on hydroxyapatite, and separating the leucotaxine preparation into anaphylatoxin and cocytotaxin proteins by chromatographic methods, the improvements comprising separating, prior to chromatography on hydroxyapatite, a major fraction of accompanying foreign blood constituents from said serum protein concentrate fraction by fractional elution and then filtering the residual protein precipitate containing anaphylatoxin and cocytotaxin by molecular sieve filtration.

16. A process according to claim 15, wherein the serum protein concentrate fraction is first fractionally eluted and the residual anaphylatoxin- and cocytotaxin-containg precipitate is then subjected twice to preparative molecular sieve filtration and once to analytical molecular sieve filtration in water or in a protein-compatible liquid.

17. A process according to claim 16, wherein the first preparative molecular sieve filtration is replaced by precipitation of foreign accompanying proteins with a water-soluble alcohol.

18. A process according to claims 15, 16 or 17 wherein for fractional elution, the serum protein concentrate fraction is adjusted to an ammonium sulfate concentration of approximately 2.6 mol/l with a protein-compatible liquid.

19. A process according to claim 18, wherein the protein-compatible liquid is a, 0.001 mol/l sodium potassium phosphate buffer containing about 0.1 mol/l NaCl and having a pH of approximately 6.3.

20. A process according to claim 16 or 17 wherein the first preparative molecular sieve filtration is carried out at a temperature of 0° to 8° C. and a pH of 6 to 8 on a hydrophilic, water-swelling molecular sieve having a separation limit of 20,000 daltons.

21. A process according to claim 16 or 17, wherein the second preparative molecular sieve filtration is carried out at a temperature of 0° to 8° C. and a pH of 6 to 8 on a hydrophilic, water-swelling molecular sieve having a separation limit of 13,000 daltons.

22. A process according to claim 16 or 17, wherein the analytical molecular sieve filtration is carried out at a temperature of 0° to 8° C. and a pH of 6 to 8 on a hydrophilic water-swelling molecular sieve with separation limits of 11,000 and 6000 daltons.

23. A process according to claim 20, wherein the molecular sieve filtration is carried out in the presence of ammonium sulfate at a concentration of up to about 0.6 mol/l.

24. A process according to claim 21, wherein the molecular sieve filtration is carried out in the presence of ammonium sulfate at a concentration of up to about 0.6 mol/l.

25. A process according to claim 20, wherein the molecular sieve filtration is carried out in the presence of cysteine at a concentration of up to about 0.001 mol/l.

26. A process according to claim 21, wherein the molecular sieve filtration is carried out in the presence of cysteine at a concentration of up to about 0.001 mol/l.

27. A process according to claim 22, wherein the molecular sieve filtration is carried out in the presence of cysteine at a concentration of up to about 0.001 mol/l.

28. A process for obtaining anaphylatoxin and cocytotaxin proteins in molecularly homogeneous, biologically active form from contact activated mammalian serum, which comprises:

separating proteins contained in said serum from other serum constituents to obtain a serum protein concentrate fraction;

removing a major part of accompanying foreign blood proteins from said protein concentrate fraction using fractional elution, precipitation with a water soluble alcohol, or molecular sieve filtration;

isolating a leucotaxine preparation from said protein concentrate fraction using hydroxyapatite chromatography;

purifying said leucotaxine preparation by a second hydroxyapatite chromatography, followed zone precipitation chromatography and finally by analytical molecular sieve filtration; and separating said purified leucotaxine preparation into anaphylatoxin or cocytotaxin.

29. The process of claim 28, wherein said purified leucotaxine preparation is separated into anaphylotoxin and cocytotaxin using cascade or recycling molecular sieve filtration.

30. A process for obtaining an anaphylatoxin and cocytotaxin containing leucotaxine preparation in biologically active form from contact activated mammalian serium, comprising:

separating serum proteins from other serum constituents to obtain a first protein concentrate;

separating a major fraction of foreign blood proteins from said serum protein concentrate by fractional elution to obtain a protein precipitate containing anaphylatoxin and cocytotaxine;

filtering said protein precipitate with molecular sieves to obtain a second protein concentration; and isolating said anaphylatoxin and cocytotaxin containing preparation from said second protein concentrate using hydroxyapatite chromatography.

31. The invention of claim 30 wherein said anaphylatoxin and cocytotaxin containing leucotaxin is separated into anaphylatoxin and cocytotaxin proteins.

32. A process for obtaining anaphylatoxin and cocytotaxin proteins in molecularly homogeneous, biologically active form from contact activated mammalian serum, comprising:

separating serum proteins from other serum constituents to obtain a first protein concentrate;

separating a major fraction of foreign blood proteins from said serum protein concentrate by fractional elution to obtain a protein precipitate containing anaphylotoxin and cocytotaxin;

filtering said protein precipitate with molecular sieves to obtain a second protein concentration;

isolating said anaphylatoxin and cocytotaxin containing preparation from said second protein concentrate using hydroxyapatite chromatography, and further purifying said preparation to obtain anaphylatoxin and cocytotaxin proteins.

* * * * *